United States Patent [19]

Nelson

[11] 4,067,760
[45] Jan. 10, 1978

[54] GATE CONTROL FOR PRINTED WEB SCANNER

[75] Inventor: Fredolf O. Nelson, Battle Creek, Mich.

[73] Assignee: General Foods Corporation, White Plains, N.Y.

[21] Appl. No.: 669,932

[22] Filed: Mar. 24, 1976

[51] Int. Cl.$^2$ .................. B65H 19/18; B65H 69/06
[52] U.S. Cl. .................................. 156/157; 156/159; 156/304; 156/361; 156/378; 156/379; 156/504; 156/505; 242/58.3; 242/58.4; 250/548
[58] Field of Search ................... 242/36, 58.1, 58.3, 242/58.4; 250/222 R, 223, 548, 561, 571; 156/157, 159, 502, 504, 505, 506, 545, 304, 351, 361, 379, 378

[56] References Cited

U.S. PATENT DOCUMENTS

| | | | |
|---|---|---|---|
| 2,536,153 | 1/1951 | Bishop | 242/58.3 |
| 3,042,332 | 7/1962 | Astley | 242/58.3 |
| 3,161,366 | 12/1964 | Bent et al. | 242/58.3 |
| 3,232,548 | 2/1966 | Bent et al. | 242/58.1 |
| 3,391,877 | 7/1968 | Angell et al. | 242/58.3 |
| 3,516,617 | 6/1970 | Haner et al. | 156/361 |
| 3,567,534 | 3/1971 | Kushiro | 156/157 |
| 3,761,177 | 9/1973 | Corse | 250/548 |
| 3,783,293 | 1/1974 | Gold et al. | 250/548 |
| 3,858,819 | 1/1975 | Butler, Jr. | 242/58.3 |

Primary Examiner—William A. Powell
Assistant Examiner—M. G. Wityshyn
Attorney, Agent, or Firm—C. Garman Hubbard; Bruno P. Struzzi; Thomas V. Sullivan

[57] ABSTRACT

A continuous clear surfaced web adapted to be fed from a supply roll thereof for a converting operation thereon is preprinted with a succession of identical repeat patterns extending over the entire width of the web. Each pattern consists of areas which contain printed matter and at least one longitudinable discontinuous area or segment which, except for the presence of a printed register mark therein, is clear and unprinted. A photo sensitive scanner is directed at the register mark track of the feeding web for detecting the register marks and controlling in accordance therewith the timing of an associated machine operation, such as web splicing, so as to be performed in register with the web pattern. The operation of the scanner is controlled by a digital reset counter of pulses fed from a pulse generator driven by the web feeding mechanism. The counter is reset to zero upon the detection of each register mark. It is initially preset to a number during the count of which the scanner is deactivated and after the count of which the scanner is activated. The number preset in the counter corresponds to the length of the register mark track starting from one register mark and continuing up to the segment of clear track containing the next register mark. The counter thus gates the operation of the scanner so as to detect only register marks and not to misread other printed matter lying in the scanned track as a register mark.

19 Claims, 8 Drawing Figures

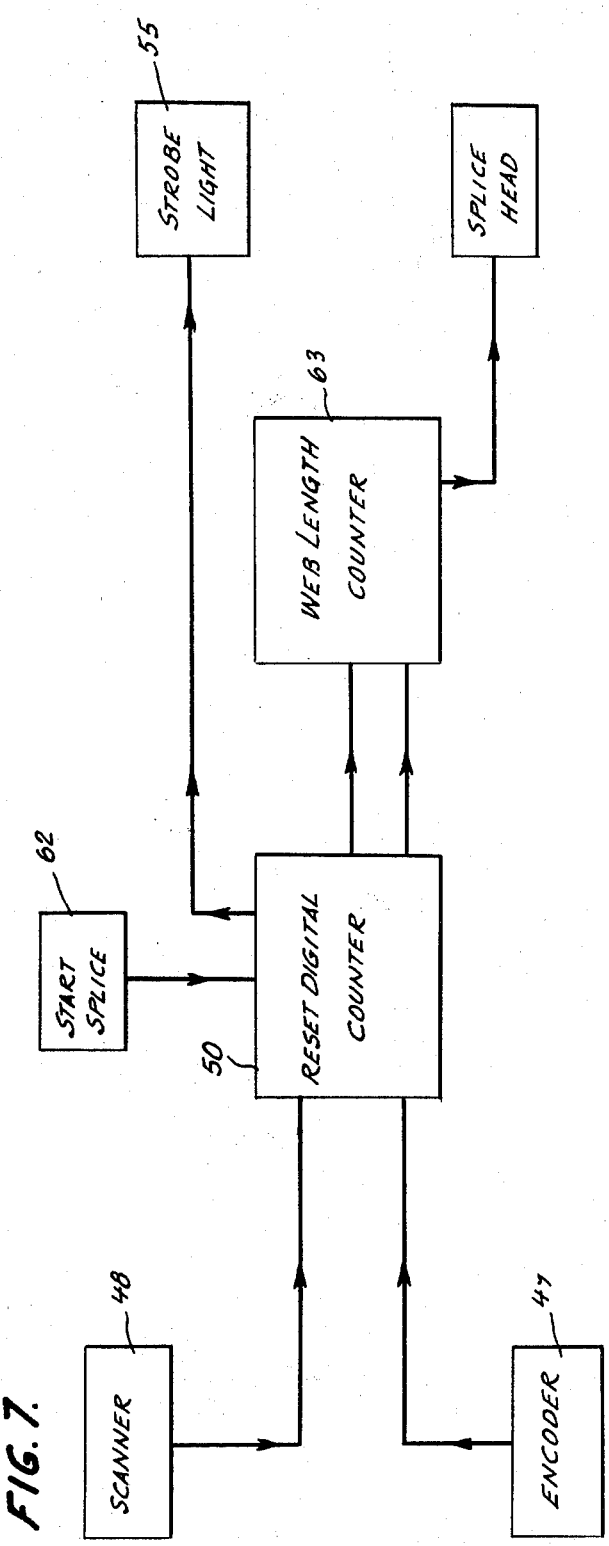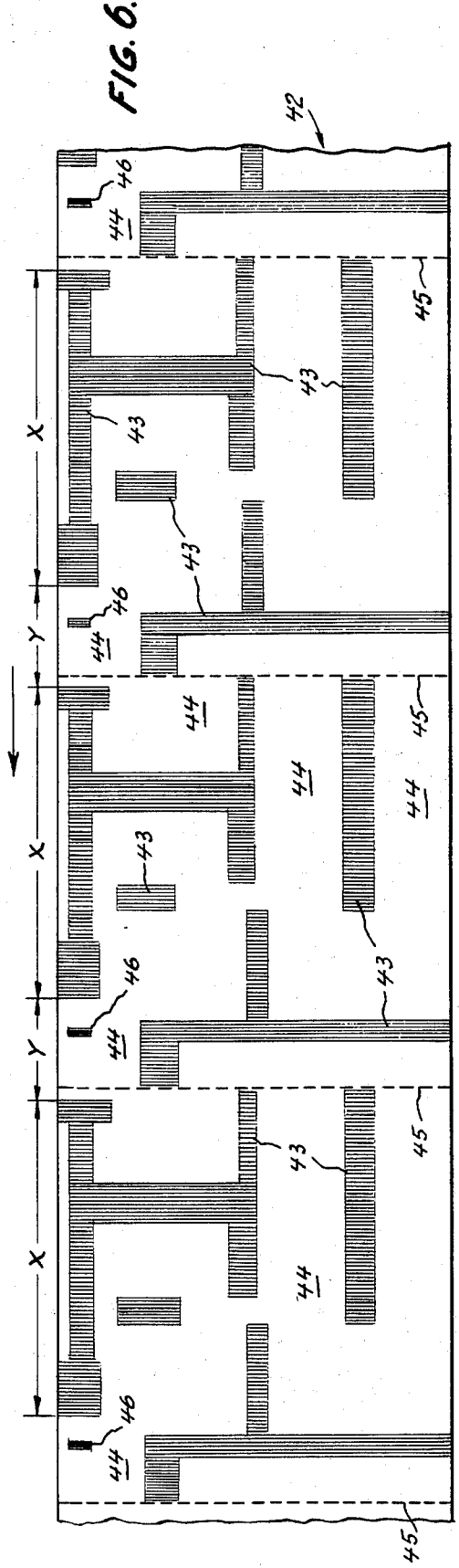

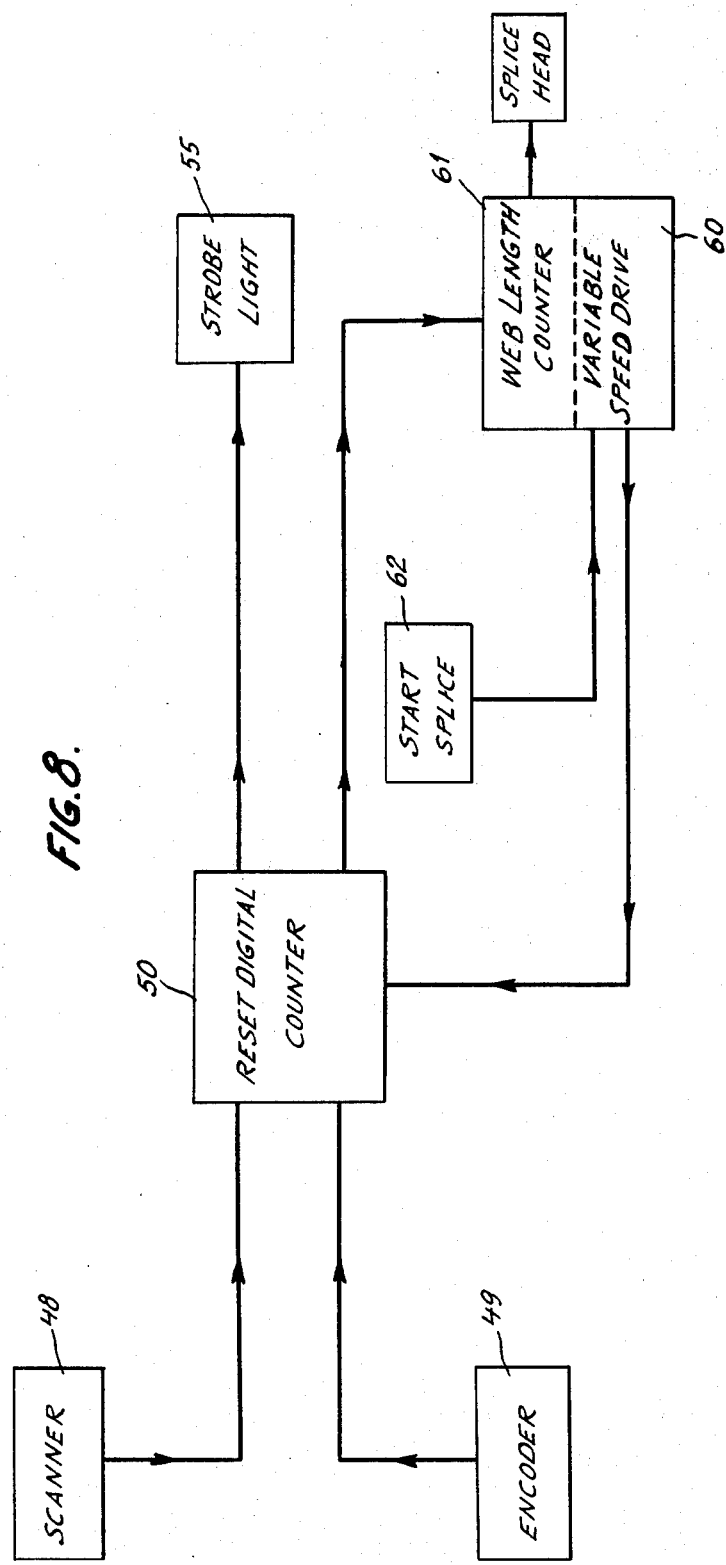

GATE CONTROL FOR PRINTED WEB SCANNER

BACKGROUND OF THE INVENTION

This invention relates generally to web handling apparatus and, more particularly, to apparatus operable on webs containing a preprinted pattern thereon and wherein it is required that the operation be performed in close register with said printed pattern. The invention is disclosed herein in an adaptation designed to splice automatically and in-register a new web of printed paperboard to an expiring web of printed paperboard being fed to carton blank die cutting equipment, for example. In equipment of this type carton blanks are die cut from the web at high speeds on a repetitive basis with very close register tolerance relative to the printed copy. Register is maintained by repetitively sensing printed register marks located at fixed repeats of the copy. Customarily, the register marks are located in an otherwise clear longitudinal track outside of the printed pattern in an area of the web reserved for that purpose. The web is automatically advanced or retarded relative to the cutting die to correct an out of register situation when it is found to occur. Just before expiration of the roll being run, the web of a new roll is spliced to the web of the expiring roll to avoid loss of the web in the feeding apparatus. The splice is normally made with the printed repeat patterns of the respective webs in-register to prevent excessive spoilage of the new web which would otherwise result in realigning the pattern thereof to register with the cutting die. Until recently, splices of this nature have been made manually requiring shut down of the equipment with consequent production loss during the down time period.

THE PRIOR ART

Fairly recently equipment has been designed for the purpose of controlling web handling apparatus so as to perform an operation in-register with the repeat pattern printed on the web. In U.S. Pat. No. 3,161,366 to Bent et al. there is disclosed a web splice control apparatus intended to achieve in-register splicing of preprinted webs automatically without interruption of web feed. In this apparatus the new roll of printed web material is supported in a position adjacent a section of the expiring web and is driven so as to have a peripheral speed approximating the linear speed of the expiring web. The register marks are printed on the webs in a track outside the printed repeat pattern, and in addition, a magnetic register mark is placed on the surface of the new roll. The printed register marks on the expiring web are scanned by a photo cell and the magnetic mark on the new web is read by a detector. When the interval between the respective scanning and detecting readouts indicates that the respective patterns are in register, the adhesive coated new web is brought into contact with the expiring web to achieve the splice. The apparatus of this patent, in addition to calling for means for driving the new roll at a surface speed approximating that of the expiring web, also requires that the webs include a clear track portion running longitudinally outside the preprinted pattern to accommodate the printed register marks. Another splicing apparatus of the same general type involving driving the new roll at a peripheral speed approximating that of the expiring web and calling for clear tracks of printed register marks on the webs is disclosed in U.S. Pat. No. 3,391,877 to Angell et al.

In U.S. Pat. No. 3,783,293 to Gold et al. there is disclosed another register control system usable in conjuction with a multi-color printing operation. This system calls for the printing of register marks in a longitudinal track outside of the printed web pattern. Photo cells operating in conjunction with a pulse generator driven by the web feed determines the correctness of register in accordance with the amount of clear space in the track between one register mark and the next.

THE PRESENT INVENTION

The present invention is distinguishable over each of the prior art patents above-mentioned in that it does not require that the printed register marks lie in a clear track running outside the printed repeat pattern of the web. Rather, by virtue of gating means effective for selectively controlling the operation of the photo electric scanner, register marks can be detected within a track running through the printed repeat patterns on the web as long as there is at least one segment of the track within each pattern which is clear and in which the register mark associated with that pattern can be located. Thus, a pattern of given dimensions can be located across the entire width of the web and the amount of extra web material heretofore otherwise required to serve as a clear track for register marks can be eliminated to achieve a corresponding saving of web material.

The present invention is further distinguished over the first two prior art patents above-mentioned directed to web splice control means in that it does not require rotating the new roll of web material and scanning both webs for register marks in order to achieve a matching or in-register condition. Rather, the leading edge of the new web is maintained, prior to the splicing operation, at a fixed position within the splicing head of the splicing equipment, and register is controlled by initiating the splicing operation in response to sensing of a register mark in only the expiring web by a photo cell which is located in known distance along the web feed path from the splicing head.

The control devices employed in accordance with the invention for achieving in-register splices are designed for use with conventional known splicing apparatus and comprise essentially a photo cell scanner, an encoder (pulse generator) and a reset counter. The scanner is disposed to read the register mark track on the old or expiring web at a point a fixed distance along the web path from the splicing head. The encoder is driven by an idler roll along the web feed path for the expiring roll or web and sends pulses to the counter. Each pulse represents a uniform increment of web length, the total number of pulses generated between detection of successive register marks being a measure of the length of the repeat pattern of the web.

Prior to a run the nominal length of the repeat pattern in terms of number of pulses is determined, this being the distance from one register mark to the next. Also the distance in terms of number of pulses from one register mark to the clear unprinted segment of register mark track in which the next register mark is located is determined. The counter is then preset with a number which is somewhat less than the total number of pulses between register marks but somewhat greater than the number representing the distance from a register mark to the clear track segment containing the next register mark. Thereafter, when the web is running, pulses are counted starting with the sensing of a register mark and the count continues until the number preset into the counter is reached indicating that the web has advanced to a position where the clear track segment containing the next register mark is in scanning position. During the count up to the preset number the counter inhibits or deactivates the scanner so that any printed matter contained in the register mark track is ignored and cannot be misread by the scanner as a register mark. As soon as a preset number is reached counting is terminated and the counter activates the scanner. Thereafter as the web continues to feed with the scanner now activated, the next register mark is detected. Detection of the register mark by the scanner signals the counter to reset, at the same time deactivating the scanner, and the cycle is repeated on a continuous basis. In this manner the action of the encoder in cooperation with the counter operates to gate the action of the scanner so as to enable the detection of register marks located in clear segments of the register mark track and to ignore or be unresponsive to any other markings which may appear in unclear segments of the register mark track. The term "clear" when used herein with reference to the web surface or a track therein means being devoid of any marks of the same or greater intensity than the printed register marks for the respective repeat web patterns.

When the old web is about to expire and a splicing operation is called for by the machine operator, the control equipment becomes conditioned so that the signal generated by detection of a following register mark acts not only to reset the counter but also to start a measure of the feed of the expiring web for a length calculated to bring the web into pattern registration with the leading edge of the new web held in the splicing head and thereupon to actuate the splicing head to achieve an in-register splice of the two webs.

It is, therefore, an object of the invention to improve upon means operable for detecting printed register marks on a moving web having other printing thereon.

It is another object of the invention to gate the operation of a printed web scanner so that it is activated only during passage of selected areas of the web past the scanner.

It is a further object of the invention to provide an improved control for web handling apparatus such that it operates on the web in register with preprinted patterns thereon.

It is a still further object of the invention to improve upon means and methods for controlling web splicing apparatus such as to achieve a splicing of two printed webs wherein the printed patterns of the respective webs are in register with one another.

Further objects of the invention together with the features contributing thereto and the advantages accuring therefrom will be apparent from the following description when read in conjunction with the drawing wherein;

FIG. 4 is an isometric view of preprinted webs joined by a splice of the type made by the form of splicing apparatus shown in FIG. 3.

FIG. 5 is an isometric view of preprinted webs containing a splice of the type made by the form of splicing apparatus shown in FIGS. 1 and 2.

FIG. 6 is a plan view of a section of printed web material showing repeat patterns printed thereon in relation to register marks also printed thereon.

FIG. 7 is a block diagram of a control circuit adapted for a splicing apparatus of the form shown in FIG. 3.

FIG. 8 is a block diagram of a control circuit adapted for splicing apparatus of the form shown in FIGS. 1 and 2.

DETAILED DESCRIPTION

Figure 1:
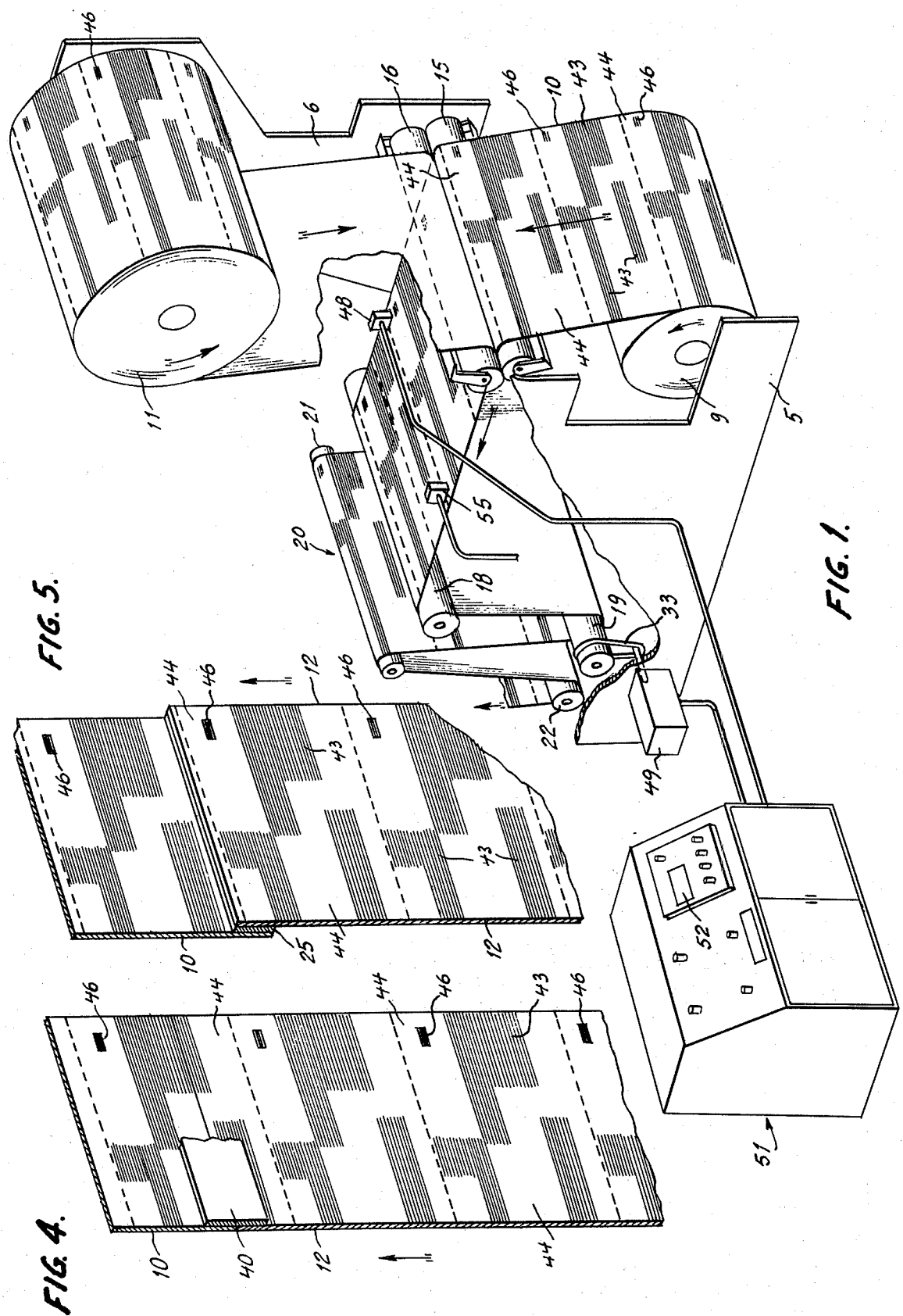
FIG. 1 is a schematic isometric view of one form of web splicing apparatus for which the invention is adapted.
Figure 2:
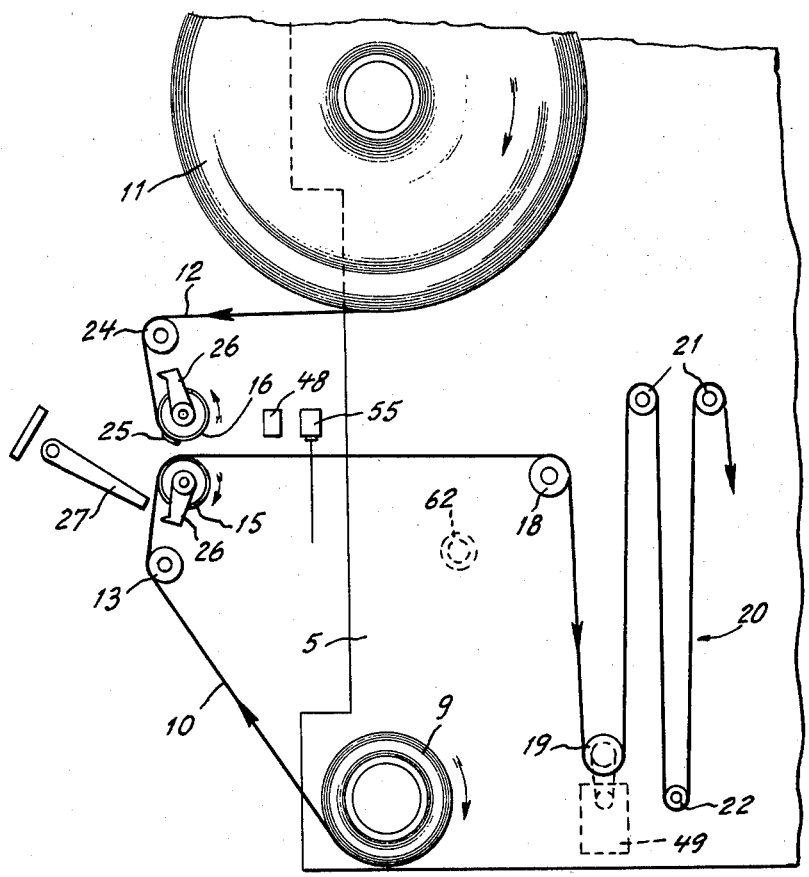
FIG. 2 is a schematic view in side elevation of the splicing apparatus shown in FIG. 1.

Referring now to the drawing, FIGS. 1 and 2 illustrate a form of web splicer which is known as The Butler Automatic Flying Splicer manufactured by Butler Automatic, Inc. of Canton, Massachusetts. As shown, the operative mechanism is mounted in framework comprised of upright side frames 5, 6. Mounted near the bottom of the framework is a roll 9 of web material 10, and mounted near the top of the framework is a roll 11 of web material 12. In the present instance, web 10 is being run through the apparatus and expiring whereas web material 12 is a fresh or new web in standby condition awaiting the next splicing operation wherein it will be attached to the trailing expired end of the web 10. However, it should be understood that the locations of the new and old rolls respectively could be reversed since the apparatus is able to operate with the new or old roll at either location. In practice, during a continuous run the respective positions are reversed alternately as a new roll is mounted in place of an expired roll at the completion of each splicing operation.

The expiring web 10, as it is unwound from spool or roll 9 runs around an idler 13, not shown in FIG. 1, and then around the lower one of a pair of nip rolls 15, 16 which function as idlers and are normally spaced apart as seen in FIG. 2. Web 10 then proceeds around idlers 18, 19 from whence it is directed into a festoon 20 comprised of opposed dancer rolls 21 and idlers 22 which operate in a known manner to maintain a supply of slack in the web which can be fed out to compensate for a reduction in the speed of web feed through the splicer, or even a temporary stopping thereof, in relation to the speed of web feed through the associated web handling apparatus to which the web is fed from the festoon.

The new web 12 as it is withdrawn from its supply roll or spool 11 is drawn around an idler 24, not shown in FIG. 1, and thence runs to the upper nip roll 16 where its leading edge is held by vacuum in readiness for the next splice. The new web 12 is first made ready by applying a length of splicing tape 25, adhesively coated on both sides, across the web at its leading edge, with the leading edge being at a point having a predetermined known relationship to the repeat pattern printed on the web. The leading edge is then affixed to the nip roll 16 as aforesaid. Upon initiation of the splicing operation or cycle, the expired web 10 is brought to a halt after being fed a predetermined known distance to bring the web into pattern registration at the nip rolls with the leading edge of the new web 12. Thereupon, the nip rolls are closed to bring the splicing tape 25 into contact with the expiring web, and the web cutter bar 26 associated with the lower nip roll 15 is actuated to cut off against an anvil 27 the remaining portion of the expiring web which falls free. Vacuum is removed from the upper nip roll 16 and web feed is resumed with the splicing tape 25 being pressed against the expiring web to provide a firm bond at the splice. The nip rolls are then separated or opened and the apparatus resumes its normal feeding function which now withdraws the new web 12 from its supply roll 11. The form of splice made by splicing apparatus just described is a lap type splice as shown in FIG. 5 with the leading edge of the new web overlapping the trailing edge of the expiring web 10, the overlapping portions of the respective webs being secured to one another by the splicing tape 25. The manner of operation of the splicing mechanism just described will be hereinafter referred to as a "stopped mode" of operation in view of the fact that splicing occurs at a time when the web feed is momentarily halted. It of course is understood that the web handling apparatus to which the web is being ultimately fed runs continuously and is not stopped, and this is possible by reason of the reason of the festoon in the web feeding system.

Figure 3:
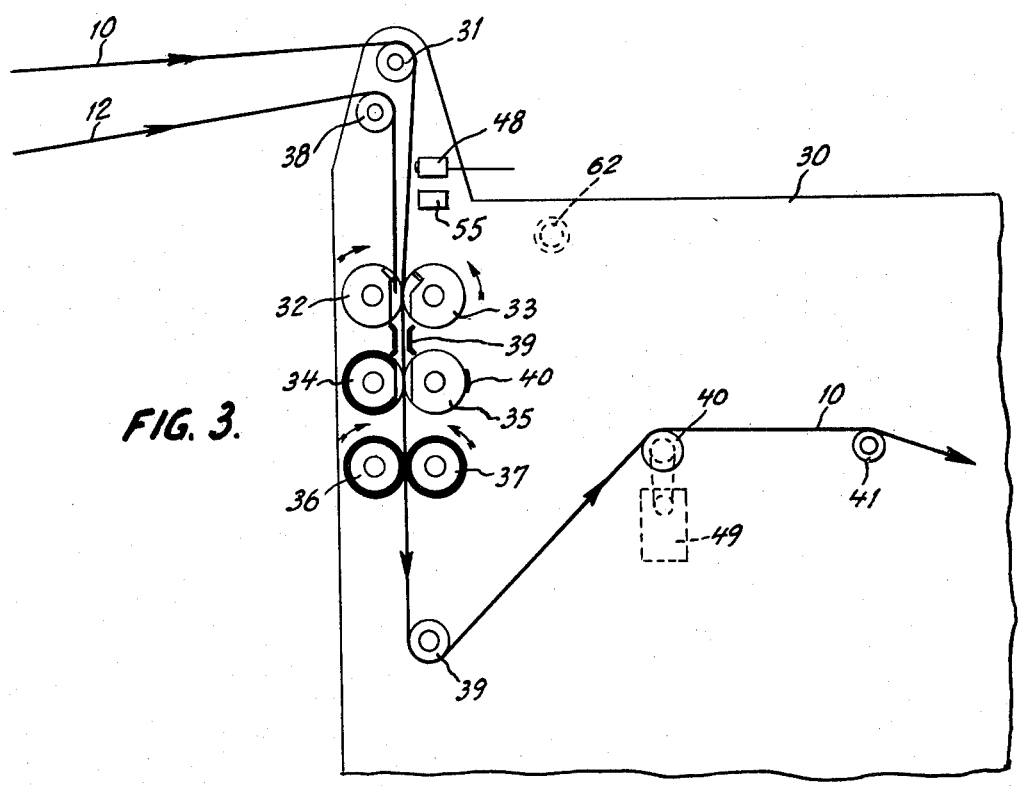
FIG. 3 is a schematic view in side elevation of another form of web splicing apparatus for which the present invention is adapted.

FIG. 3 illustrates another form of splicing apparatus for which the control means of the present invention is adapted and which functions in accordance with what will be referred to as a "moving mode" of operation. As shown in FIG. 3 an expiring web 10 withdrawn from a supply roll, not shown, is fed over an idler roll 31 suitably supported in the frame 30 of the apparatus. The web 10 then runs through the splicing head which is comprised of a pair of opposed cut-off rolls 32, 33 followed by a pair of opposed taping rolls 34, 35 which are in turn followed by a pair of pull rolls 36, 37. The tape thence proceeds from the splicing head around idler rolls 39, 40, 41 as it proceeds to other web handling devices operable thereon, not shown. The cut off rolls 32, 33 are normally stationary and are formed with opposed chordal segments or flat areas in their surfaces so as to provide a gap through which the web may feed unrestrictedly. The taping rolls 34, 35 are similarly normally inactive and formed with a flat chordal segment on opposing surfaces to provide a gap for the feeding web. The pull rolls 36, 37 are continuously driven and operate to pull the web through the splicing head.

The new web 12 runs from its supply roll or spool, not shown, around an idler roll 38 and up to the gap between the cut off rolls 32, 33 where the leading edge thereof, at a predetermined known location in relation to the repeat pattern printed on the web, is held by a clip mechanism, not shown, carried by the roll 32. The splice is accomplished by activating the rolls 32, 33 and the rolls 34, 35 for one revolution, at the same speed as the pull rolls 36, 37, through a one revolution clutching mechanism. During the revolution of the cut off rolls a knife edge carried by roll 33 in cooperation with a cutting anvil carried by the roll 32 cuts through both webs to thereby cut off the expiring portion of the old web 10 and at the same time trim off the leading edge of the new web 12 along a line of cut in precise alignment with the line of cut in the expiring web 10. The new web 12 remains in the grip of the rolls 32, 33 and as they continue to rotate through one revolution the leading edge of the web 12 is directed through a web guide 39 to the nip between rolls 34, 35. At the time the aligned cut edges of the respective webs reach the nip rolls 34, 35 they will have rotated about one-half revolution and will act to place a length of splicing tape 40, coated with adhesive on its outer surface and previously applied to the roll 35, over the cut edges of the respective webs under pressure provided by the opposed roll 34 so as to thereby join the respective webs in a butt type of splice such as is shown in FIG. 4. As the cut off rolls and taping rolls complete their one revolution of rotation the flat surfaces thereon again are place in opposed relationship to one another providing a gap through which the new web 12 now feeds by the continuous operation of the pull rolls 36, 37. It will be noted that splicing is achieved in this "moving mode" of operation without stopping the feed of the expiring web 10 and thus enables the web handling apparatus to which the web is ultimately fed to operate continuously without need for a festoon device between it and the splicing apparatus. Conventional commercially available splicing apparatus operating according to this "moving mode" concept is known as the Inta Roto Butt Splicer manufactured by Inta Roto Incorporated located in Richmond, Va. At the instant a splicing cycle is initiated, at which time the location of a printed repeat pattern on the expiring web in relation to the splicing head is known, a measurement of the amount of web fed to the splicing head is started and continues until the measurement reaches the amount of web calculated to bring the printed pattern of the expiring web in register with the printed pattern of the new web at the splicing head, whereupon the splicing head is actuated to join the two webs in a splice wherein the patterns of the respective webs are in register with one another.

FIG. 6 illustrates in plan a length of web 42 having a plurality of typical repeat patterns printed thereon. The shaded portions 43 represent printed portions of the repeat pattern of various configurations and which may comprise lettering, coloring or designs of varied sorts. The unshaded areas 44 represent clear unprinted portions of the web repeat patterns. Three complete repeat patterns are illustrated and the repeat length of a pattern is indicated by the web area lying between broken lines 45.

As shown, register marks 46, of which there is one in fixed relation to each repeat pattern, may be in the form of a solid or dark printed rectangle. The marks are in alignment longitudinally near one edge of the web and lie in what may be considered a register mark track. The track thus runs longitudinally of the web through the successive repeat patterns and will be seen to comprise unclear track segments X by virtue of printed matter 43 lying therein and clear track segments Y by virtue of there being no printing therein other than the register mark itself. The web printing shown in FIGS. 1, 4 and 5, while not identical in configuration to that shown in FIG. 6, is for all practical purposes of the invention similar in that it will be seen to include register marks 46 lying in a register mark track running longitudinally of the webs through both printed and unprinted portions of the respective patterns with the mark itself located in a clear unprinted portion of the respective patterns.

The control devices which function to gate the scanning operation include a scanner 48 and an encoder (pulse generator) 49 both electrically connected to a reset digital counter 50 having a readout display and suitably housed in a control console 51. The console is provided with appropriate control knobs by which power may be turned on and off, the web may be jogged, the counter manually reset, the counter manually preset to a number for timing the gating action of the scanner, and includes a window 52 through which the number of pulses entered in the counter can be viewed. The scanner 48, in the "stopped mode" form of splicing apparatus shown in FIGS. 1 and 2, is positioned above the feeding web 10 at a point beyond the nip rolls 15, 16 constituting the splicing head and a known distance therefrom. The scanner is in alignment with the register mark track of the web and is directed thereto. The encoder 49 is suitably mounted on the frame of the machine and is coupled by a drive belt 33 with the shaft for idler roll 19 so as to continuously emit a series pulses representing increments of web feed length as long as the apparatus is operating.

Prior to a web feeding operation it will be understood that the control portion of the timer has been preset with a number representing in terms of pulses a distance less than the repeat length of the printed web pattern but greater than the distance from one register mark to the clear track segment Y in which the next register mark is located. Thus, with reference also to FIG. 6 and assuming that web feed is started with a register mark 46 under the scanner and the counter reset to zero, as the web starts to move the counter will start counting pulses received from encoder 49, but the scanner will not be active since it is inhibited during the counting portion of the scanning cycle. Thus, the remainder of the Y segment of the register mark track in which the register mark is located will not be scanned and as feeding continues the next X segment of the track comes under the scanner but no printed matter therein can be read since the scanner remains inhibited. A short time after the next Y segment reaches the scanner the counter will have reached the number preset therein and counting will terminate with the count holding and with the scanner now activated. When the register mark 46 in said next Y segment reaches the scanner, it is detected to generate a scanning pulse which is effective for resetting the counter. Reset of the counter deactivates the scanner. As web feed continues the counter again starts counting with the scanner deactivated, and the scanning cycle thus repeats on a continuous basis.

It will be seen that the scanning system allows for minor variations in the length of the repeat pattern due to web shrinkage or stretching since a number can be selected for preset into the counter control such as to activate the scanner when scanning any part of the clear Y track segment preceding the register mark. It does not require that the scanner be activated at any precise point in the register mark track.

A related monitoring function may be achieved by provision of a strobe light 55 positioned over the feeding web at or about the same point in the feed path as the scanner 48. The lamp is directed onto the register mark or some other recognizable mark in the print pattern and is energized by the counter when reset upon receiving a scan signal. Thus the machine operator on viewing the part of the web illuminated by the strobe at the time a register mark is detected by the scanner can determine whether the web patterns are in phase with the scanner mechanism. If not in phase, correction can usually be achieved by manually resetting the counter.

When controlling a "stopped mode" type of splicing apparatus to achieve an in-register splice the operation is as follows. First it should be understood that this type of splicing apparatus is provided with a variable speed drive 60 or stepping motor, such as made by WER Industrial, a division of Emerson Electric Co., of Buffalo, N.Y., which operates in conjunction with appropriate braking means, not shown, to slow down the speed of the feeding web to a predetermined rate in preparation for a full stop of the web for completion of the splicing cycle. Also, associated with the drive 60 is a web length counter 61 which upon signal starts to measure the amount of web feeding to the splice head and stops the feed after determining that the measured amount has been fed. When the machine operator determines that a splice is required the operation is initiated by pressing a start splice button 62 which signals the variable speed drive mechanism 60 of the apparatus to start slowing down in preparation for the start of a splicing cycle. When the drive has slowed down to the predetermined rate the drive mechanism signals the counter 50 to condition itself to signal the web length counter 61 upon receipt of the next pulse from scanner 48. Receipt of this pulse by the web length counter 61 can be considered as starting the actual splice cycle of the apparatus whereupon the web length counter 61 starts measuring the web feeding to the splice head. Since the signal is received at the time a register mark is under the scanner 48, whereby the position of the repeat pattern relative to the splice head is known, the measured amount of web fed under control of the web length counter 61 is calculated to bring the repeat pattern of the expiring web 10 into pattern registration with the new web 12 as the feeding web is brought to a complete stop. Thereupon the web length counter sends an activating signal to the splice head which operates as aforesaid to join the two webs together in a lap splice with the patterns of the respective webs in register with one another.

With reference now to FIGS. 3 and 7, it will be seen that in the adaptation of the invention to a "moving mode" form of splicing apparatus the gating of the scanning function operates in the same manner as just described with reference to the "stopped mode" form of apparatus. In this case, the scanner 48 and strobe light 55 are disposed along the feed path of web 10 at a position slightly before the web enters the splicing head comprising the cut-off rolls 32, 33 and taping rolls 34, 35. The encoder 49 in this instance is mounted on the frame 30 and is driven from the shaft carrying idler roll 40. It will be understood that the scanner, strobe light and encoder are electrically connected to a reset digital counter 50 contained in a control console, not shown in FIG. 3, but which operates in the same manner as heretofore described to gate the scanner so as to ignore unclear segments of the register mark track and to pulse the strobe light 55 so as to enable the phase of the web pattern in relation to the scanner to be monitored.

In this form of the invention, the start splice button is electrically connected directly to the reset digital counter 50 and when pushed by the operator to start a splicing operation is effective for conditioning the counter 50, when reset by the next scanner pulse, to signal a web length counter 63 to start a measurement of the web feeding to the splice head, the counter 63 being at the same time connected to the encoder 49 to enable said measurement. This instant may be considered the start of the splice cycle and occurs at the instant a register mark is under the scanner at which time the relation of the repeat pattern on the web to the splicing head is known. The web length counter 63, after measuring the length of web calculated to bring the pattern thereon in register with a pattern of the new web at the splicing head, signals the splice head to activate and effect the butt type splice with the respective web patterns in register.

While there has been shown and described what is considered to be preferred embodiments of the invention, it will of course be understood that many changes in form and detail could be made to the apparatus herein shown and described without departing from the spirit of the invention. It is, therefore, intended that the invention be not limited to the exact form and details herein shown and described nor to anything less than the whole of the invention as hereinafter claimed.

What is claimed is:

1. Apparatus for detecting register marks in clear portions of a track running through clear and unclear portions of repeat patterns on a moving web comprising:
   a. a scanner positioned adjacent said web and operable for emitting a scanning pulse upon detection of a register mark in the track of the moving web;
   b. an encoder driven in synchronism with the movement of said web for emitting pulses representing increments of web feed length; and
   c. a reset digital counter connected to said encoder and said scanner and responsive to receipt of a predetermined number of pulses from said encoder to gate the operation of said scanner to inhibit scanning of unclear track portions while counting up to said predetermined number and to enable scanning of clear track portions upon reaching said predetermined number, said counter being reset and said scanner being deactivated upon receipt of a scanning pulse.

2. The invention according to claim 1 wherein said predetermined number is a number less than the number of pulses representing the distance between successive register marks and greater than the number of pulses representing the distance from a register mark to the clear track portion containing the next register mark.

3. The invention according to claim 2 wherein said scanner is a photo electric cell and said register mark is a printed designation within a clear track portion, and wherein the unclear track portions contain printing of subject matter other than a register mark.

4. The invention according to claim 3 including;
   d. a strobe light positioned adjacent to said moving web and directed to recognizable printed matter on the surface of said web at pattern repeat length distances along the web said light being energized in response to detection of a register mark by said scanner for monitoring the phase relationship between said repeat patterns and said scanner.

5. Apparatus for splicing web material feeding to web handling mechanism and having register marks located in clear portions of a track running through clear and unclear portions of repeat patterns thereon, said apparatus including a splicing head operable during a splicing cycle to join an expiring web at said splicing head with the leading edge of a new web located at said splicing head comprising:
   a. a scanner positioned adjacent said expiring web a fixed distance from said splicing head for emitting a scanning pulse upon detection of a register mark in the track of said expiring web;
   b. an encoder driven in synchronism with the feed of said expiring web for emitting pulses representing increments of web feed length; and
   c. a reset digital counter connected to said encoder and said scanner and responsive to receipt of a predetermined number of pulses from said encoder for gating the operation of said scanner to inhibit scanning of unclear track portions while counting up to said predetermined number and to enable scanning of clear track portions upon reaching said predetermined number, said counter being reset by receipt of a scanning pulse to deactivate said scanner and conditionable to initiate a splicing cycle when reset by receipt of a scanning pulse.

6. The invention according to claim 5 wherein said predetermined number is a number less than the number of pulses representing the distance between successive register marks and greater than the number of pulses representing the distance from a register mark to the clear track portion containing the next register mark.

7. The invention according to claim 6 wherein said scanner is a photo electric cell and said register mark is a printed designation within a clear track portion, and wherein the unclear track portions contain printing of subject matter other than a register mark.

8. Apparatus for splicing web material feeding to web handling mechanism and having register marks located in clear portions of a track running through clear and unclear portions of repeat patterns thereon, said apparatus including a splicing head operable during a splicing cycle to join an expiring web at said splicing head with the leading edge of a new web located at said splicing head comprising:
   a. a scanner positioned adjacent said expiring web a fixed distance from said splicing head for emitting a scanning pulse upon detection of a register mark in the track of said expiring web;
   b. an encoder driven in synchronism with the feed of said expiring web for emitting pulses representing increments of web feed length;
   c. a reset digital counter connected to said encoder and said scanner and responsive to receipt of a predetermined number of pulses from said encoder for gating the operation of said scanner, said predetermined number being a number less than the number of pulses representing the distance between successive register marks to inhibit the scanning of unclear track portions while counting up to said predetermined number and to enable scanning of clear track portons upon reaching said predetermined number, said counter being reset by receipt of a scanning pulse to deactivate said scanner and conditionable to initiate a splicing cycle when reset by receipt of a scanning pulse; and
   d. a second digital counter activated at the start of a splicing cycle to measure the expiring web feeding to said splicing head and effective to activate said splicing head after the feed of a measured length of expiring web calculated to bring the reset patterns on the respective webs in register with one another.

9. The invention according to claim 8 wherein said second counter is activated to start a splicing cycle by said reset digital counter upon being reset by receipt of a scanning pulse.

10. The invention according to claim 8 wherein the feed of said expiring web is halted after being fed said measured length and prior to activation of said splicing head.

11. The invention according to claim 8 wherein the feed of said expiring web is continuous and uninterrupted by the activation of said splicing head.

12. A method for detecting register marks in clear portions of a track running through clear and unclear portions of repeat patterns on a moving web comprising the steps of:
   a. directing said web past a scanner aligned with said track and adapted to emit a scanning pulse upon detecting a register mark therein;

b. generating pulses synchronized with web movement whereby each pulse represents an increment of web feed length;

c. using a reset digital counter for counting said pulses up to a predetermined number which is less than the number of pulses representing the distance between successive register marks and greater than the number of pulses representing the distance from a register mark to the clear track portion containing the next register mark;

d. inhibiting said scanner during said counting;

e. enabling said scanner to scan clear portions after completing said counting; and f. resetting said counter and deactivating said scanner upon receipt of a scanning pulse.

13. The invention according to claim 12 wherein said counting is repeated upon detection of a register mark by said scanner.

14. The invention according to claim 12 including the step of:

f. momentarily illuminating a recognizable portion of a said web upon detection of a register mark to enable the phase relationship between said repeat patterns and said scanner to be monitored.

15. A method for controlling apparatus adapted to splice feeding web material having register marks located in clear portions of a track running through clear and unclear portions of repeat patterns thereon, said apparatus including a splicing head operable during a splicing cycle to join an expiring web at said splicing head with the leading edge of a new web located at said splicing head comprising the steps of:

a. directing said expiring web past a scanner aligned with said track and adapted to emit a scanning pulse upon detecting a register mark therein;

b. generating pulses synchronized with web movement whereby each pulse represents an increment of web feed length;

c. using a reset digital counter for counting said pulses up to a predetermined number which is less than the number of pulses representing the distance between successive register marks and greater than the number of pulses representing the distance from a register mark to the clear track portion containing the next register mark;

d. inhibiting said scanner during said counting;

e. enabling said scanner to scan clear portions upon completion of said counting;

f. resetting said counter to deactivate said scanner and repeat said counting upon detection of a register mark by said scanner; and g. initiating a splicing cycle at the moment a selected register mark is detected by said scanner.

16. The invention according to claim 15 wherein said splicing head is activated after a predetermined length of the expiring web has been fed to said splicing head following the initiation of the splicing cycle.

17. A method for controlling apparatus adapted to splice feeding web material having register marks located in clear portions of a track running through clear and unclear portions of repeat patterns thereon, said apparatus including a splicing head operable during a splicing cycle to join an expiring web at said splicing head with the leading edge of a new web at said splicing head comprising the steps of:

a. directing said expiring web past a scanner aligned with said track and adapted to emit a scanning pulse upon detecting a register mark therein;

b. generating pulses synchronized with web feed whereby each pulse represents an increment of web feed length;

c. using a reset digital counter for counting said pulses up to a predetermined number which is less than the number of pulses representing the distance between successive register marks and greater than the number of pulses representing the distance from a register mark to the clear track portion containing the next register mark;

d. inhibiting said scanner during said counting;

e. enabling said scanner to scan clear portions after completing said counting;

f. resetting said counter to deactivate said scanner and repeat said counting upon detection of a register mark by said scanner;

g. measuring the feed of the expiring web to the splicing head from the moment a selected register mark is detected by said scanner; and h. activating said splicing head after feed of a measured length of said expiring web calculated to bring a pattern on the expiring web in register with a pattern of the new web at the splicing head.

18. The invention according to claim 17 wherein the feeding of said expiring web is stopped after the feeding of said measured length and before activation of said splicing head.

19. The invention according to claim 17 wherein the feed of the expiring web is continuous and uninterrupted during the activation of the splicing head.

* * * * *